US007230025B2

(12) United States Patent
Barba et al.

(10) Patent No.: US 7,230,025 B2
(45) Date of Patent: Jun. 12, 2007

(54) PYRAZOLE DERIVATIVES

(75) Inventors: Oscar Barba, Ramsgate (GB); Lyn Howard Jones, Canterbury (GB)

(73) Assignee: Pfizer, Inc., New York, NY (US)

( * ) Notice: Subject to any disclaimer, the term of this patent is extended or adjusted under 35 U.S.C. 154(b) by 366 days.

(21) Appl. No.: 10/669,812

(22) Filed: Sep. 23, 2003

(65) Prior Publication Data

US 2004/0110816 A1 Jun. 10, 2004

Related U.S. Application Data

(60) Provisional application No. 60/433,402, filed on Dec. 13, 2002.

(30) Foreign Application Priority Data

Sep. 26, 2002 (GB) ................................. 0222374.1
Oct. 8, 2002 (GB) ................................. 0223356.7

(51) Int. Cl.
C07D 43/02 (2006.01)
A61K 31/416 (2006.01)
(52) U.S. Cl. ................. 514/407; 548/364.1; 548/366.1
(58) Field of Classification Search ................ 514/407; 548/364.1, 366.1
See application file for complete search history.

(56) References Cited

U.S. PATENT DOCUMENTS 3,303,200 A 2/1967 Wolf et al.
5,189,040 A * 2/1993 Ohsumi et al. ............. 514/269

FOREIGN PATENT DOCUMENTS

| EP | 0 208 874 | 5/1986 |
| EP | 0 459 333 A1 | 12/1991 |
| EP | 0 649 056 A2 | 10/1994 |
| EP | 0 658 806 A1 | 10/1994 |
| GB | 1 140 898 A | 1/1969 |
| GB | 0222374.1 | 9/2002 |
| GB | 0223356.7 | 10/2002 |
| JP | 62149617 | 3/1987 |
| JP | 01 125379 | 5/1989 |
| JP | 03 141276 | 6/1989 |
| WO | WO 89/10925 | 11/1989 |
| WO | WO 91/11172 A1 | 8/1991 |
| WO | WO 94/02518 A1 | 2/1994 |
| WO | WO 98/55148 A1 | 12/1998 |
| WO | WO 02/04424 A1 | 1/2002 |
| WO | WO 02/30907 A1 | 4/2002 |

OTHER PUBLICATIONS

U.S. Appl. No. 60/433,402, filed Dec. 13, 2002, Pfizer, Inc.
Berge, Stephen M., et al., "Pharmaceutical Salts," *J.Pharm.Sci.*, 1977, pp. 1-19, vol. 66 No. 1.
Bighely, Lyle D., et al., "Salt Forms of Drugs and Absorption," *Encyclopedia of Pharmaceutical Technology*, 1996, pp. 453-497, vol. 13, Marcel Dekker Inc., New York, USA.
Bundgarrd, Hans, ed., "Design of prodrugs: Bioreversible derivative for various functional groups and chemical entitites," 1985, *Design of Prodrugs*, Chapter 1, pp. 1-92, Elsevier Science Publishers Biomedical Division.
Coppola, Gary M., et al., "Pyrimindones. 2. Synthesis and Reactions of 2-Chloropyrimidines," *J.Het.Chem*, 1980, pp. 1479-1482, vol. 17(7).
Ferres, Harry, "Pro-Drugs of β-Lactam Antibiotics," *Drugs of Today*, pp. 499-538, 1983, vol. 19, No. 9.
Genin, Michael J., et al., "Novel 1,5-Diphenylpryazole Non-nucleoside HIV-1 Reverse Transcriptase Inhibitors with Enhanced Activity versus the Delavirdine-Resistant P236L Mutant: Lead Identification and SAR of 3- and 4-Substituted Derivatives," *J.Med. Chem*, 2000, pp. 1034-1040, vol. 43.
Greene, Theodora W., et al., "Protective Groups in Organic Synthesis," 1991, 2nd Edition, John Wiley & Sons, Inc., New York, USA.
Katritsky, Alan R., FRS, et al., "Comprehensive Heterocyclic Chemistry, The Structure, Reactions, Synthesis and Uses of Heterocyclic Compounds," 1984, Pergamon Press, New York, USA.
Boeckman, Robert K., Jr., "A Novel Route to 2,3-Pyrazol-1(5H)-ones via Palladium-Catalyzed Carbonylation of 1,2-Diaza-1,3-butadienes," *Organic Letters*, 2001, 3651-3653, vol. 3, No. 23.
Hendess, Raymond W., "1-Phenyl-2-acyl-3-amino-2-pyrazolin-5-ones from 1-Phenyl-3-azidocarbonyl-2-pyrazolin-5-ones," *Journal of Organic Chemistry*, 1972, 2400-2401, vol. 37, No. 15.

* cited by examiner

*Primary Examiner*—Kamal A. Saeed
(74) *Attorney, Agent, or Firm*—Keith D. Hutchinson; Bryan C. Zielinski

(57) ABSTRACT

This invention relates to pyrazole derivatives of formula (I)

(I)

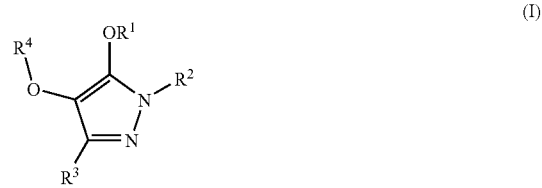

or pharmaceutically acceptable salts, solvates or derivative thereof, wherein $R^1$ to $R^4$ are defined in the description, and to processes for the preparation thereof, intermediates used in their preparation of, compositions containing them and the uses of such derivatives. The compounds of the present invention bind to the enzyme reverse transcriptase and are modulators, especially inhibitors thereof. As such the compounds of the present invention are useful in the treatment of a variety of disorders including those in which the inhibition of reverse transcriptase is implicated. Disorders of interest include those caused by Human Immunodeficiency Virus (HIV) and genetically related retroviruses, such as Acquired Immune Deficiency Syndrome (AIDS).

4 Claims, No Drawings

PYRAZOLE DERIVATIVES

This application claims priority from United Kingdom application number 0222374.1, filed Sep. 26, 2002, United Kingdom application number 0223356.7, filed Oct. 8, 2002 and also claims the benefit of U.S. Provisional Application No. 60/433,402, filed Dec. 13, 2002, and incorporates each application by reference in its entirety.

BACKGROUND OF THE INVENTION

This invention relates to pyrazole derivatives, to their use in medicine, to compositions containing them, to processes for their preparation and to intermediates used in such processes.

Reverse transcriptase is implicated in the infectious lifecycle of Human Immunodeficiency Virus (HIV). Compounds which interfere with the function of this enzyme have shown utility in the treatment of conditions caused by HIV and genetically related retroviruses, such as Acquired Immune Deficiency Syndrome (AIDS). There is a constant need to provide new and better modulators, especially inhibitors, of HIV reverse transcriptase, since the virus is able to mutate, becoming resistant to the effects of known modulators.

Antiviral activity is ascribed to a class of N(hydroxyethyl) pyrazole derivatives in U.S. Pat. No. 3,303,200. A number of pyrazoles are disclosed as reverse transcriptase inhibitors, including: a class of N-phenylpyrazoles (*J. Med. Chem.*, 2000, 43, 1034); a class of C and S linked aryl pyrazoles (WO02/04424); and a class of O and S linked aryl pyrazoles, the O and S aryl link being adjacent to the nitrogen atom (WO02/30907).

SUMMARY OF THE INVENTION

According to the present invention there is provided a compound of formula (I)

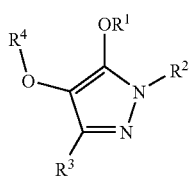

(I)

or a pharmaceutically acceptable salt, solvate or derivative thereof, wherein:

$R^1$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, OR$^{11}$, —NR$^5$R$^5$, —(C$_1$–C$_6$ alkylene)-NR$^5$R$^5$, R$^7$ or R$^{11}$;

$R^2$ is H, C$_1$–C$_6$ alkyl, C$_3$–C$_6$ alkenyl, C$_3$–C$_6$ alkynyl, C$_3$–C$_7$ cycloalkyl, C$_3$–C$_7$ cycloalkenyl, phenyl, benzyl, R$^8$ or R$^9$, said C$_1$–C$_6$ alkyl, C$_3$–C$_7$ cycloalkyl, phenyl and benzyl being optionally substituted by halo, —OR$^5$, —OR$^{10}$, —CN, —CO$_2$R$^7$, —OCONR$^5$R$^5$, —CONR$^5$R$^5$, —C(=NR$^5$)NR$^5$OR$^5$, —CONR$^5$NR$^5$R$^5$, —NR$^6$R$^6$, —NR$^5$R$^{10}$, —NR$^5$COR$^5$, —NR$^5$COR$^8$, —NR$^5$COR$^{10}$, —NR$^5$CO$_2$R$^5$, —NR$^5$CONR$^5$R$^5$, —SO$_2$NR$^5$R$^5$, —NR$^5$SO$_2$R$^5$, —NR$^5$SO$_2$NR$^5$R$^5$, R$^8$ or R$^9$;

$R^3$ is H, C$_1$–C$_6$ alkyl, C$_3$–C$_7$ cycloalkyl, phenyl, benzyl, halo, —CN, —OR$^7$, —CO$_2$R$^5$, —CONR$^5$R$^5$, R$^8$ or R$^9$, said C$_1$–C$_6$ alkyl, C$_3$–C$_7$ cycloalkyl, phenyl and benzyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, R$^8$ or R$^9$;

$R^4$ is phenyl, naphthyl or pyridyl, each being optionally substituted by R$^8$, halo, —CN, C$_1$–C$_6$ alkyl, C$_1$–C$_6$ haloalkyl, C$_3$–C$_7$ cycloalkyl, C$_1$–C$_6$ alkoxy, —CONR$^5$R$^5$, OR$^{11}$, So$_x$R$^6$, O—(C$_1$–C$_6$ alkylene)-CONR$^5$R$^5$, O—(C$_1$–C$_6$ alkylene)-NR$^5$R$^5$, or O—(C$_1$–C$_6$ alkylene)-OR$^6$;

each $R^5$ is independently either H, C$_1$–C$_6$ alkyl or C$_3$–C$_7$ cycloalkyl or, when two R$^5$ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by C$_1$–C$_6$ alkyl or C$_3$–C$_7$ cycloalkyl;

each $R^6$ is independently either H, C$_1$–C$_6$ alkyl or C$_3$–C$_7$ cycloalkyl;

$R^7$ is C$_1$–C$_6$ alkyl or C$_3$–C$_7$ cycloalkyl;

$R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, fluoro(C$_1$–C$_6$)alkyl or C$_3$–C$_7$ cycloalkyl;

$R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, C$_1$–C$_6$ alkyl, C$_3$–C$_7$ cycloalkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN;

$R^{10}$ is C$_1$–C$_6$ alkyl substituted by R$^8$, R$^9$, —OR$^5$, —CONR$^5$R$^5$, —NR$^5$COR$^5$ or —NR$^5$R$^5$;

$R^{11}$ is phenyl optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, halo(C$_1$–C$_6$)alkyl or C$_3$–C$_7$ cycloalkyl; and x is 0, 1 or 2.

In the above definitions, halo means fluoro, chloro, bromo or iodo. Unless otherwise stated, alkyl, alkenyl, alkynyl, alkylene and alkoxy groups containing the requisite number of carbon atoms can be unbranched or branched chain. Examples of alkyl include methyl, ethyl, n-propyl, i-propyl, n-butyl, i-butyl, sec-butyl and t-butyl. Examples of alkenyl include ethenyl, propen-1-yl, propen-2-yl, propen-3-yl, 1-buten-1-yl, 1-buten-2-yl, 1-buten-3-yl, 1-buten-4-yl, 2-buten-1-yl, 2-buten-2-yl, 2-methylpropen-1-yl or 2-methylpropen-3-yl. Examples of alkynyl include ethynyl, propyn-1-yl, propyn-3-yl, 1-butyn-1-yl, 1-butyn-3-yl, 1-butyn-4-yl, 2-butyn-1-yl. Examples of alkylene include methylene, 1,1-ethylene, 1,2-ethylene, 1,1-propylene, 1,2-propylene, 2,2-propylene and 1,3-propylene. Examples of alkoxy include methoxy, ethoxy, n-propoxy, i-propoxy, n-butoxy, i-butoxy, sec-butoxy and t-butoxy. Examples of cycloalkyl include cyclopropyl, cyclobutyl, cyclopentyl, cyclohexyl and cycloheptyl. Where $R^1$ and $R^2$ are taken together, they form, along with the nitrogen atom and the carbon atom of the pyrazole ring to which they are attached, a 5- or 6-membered ring. Where a heterocyclic group $R^8$ or $R^9$ is attached to an oxygen, sulphur or nitrogen heteroatom the heterocyclic group $R^8$ or $R^9$ must be linked through a ring carbon atom. Further, where a heterocyclic group $R^9$ is attached to an oxygen, sulphur or nitrogen heteroatom the heterocyclic group $R^9$ must be linked through a ring carbon atom that is not adjacent to a ring heteroatom.

The pharmaceutically acceptable salts of the compounds of formula (I) include the acid addition and the base salts thereof.

Suitable acid addition salts are formed from acids which form non-toxic salts and examples are the hydrochloride, hydrobromide, hydroiodide, chloride, bromide, iodide, sulphate, bisulphate, nitrate, phosphate, hydrogen phosphate, acetate, fumarate, pamoate, aspartate, besylate, carbonate, bicarbonate/, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts.

Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts.

For reviews on suitable salts see Berge et al, J. Pharm. Sci., 66, 1–19, 1977 and Bighley et al, Encyclopedia of Pharmaceutical Technology, Marcel Dekker Inc, New York, 1996, Vol 13, pp 453–497

The pharmaceutically acceptable solvates of the compounds of formula (I) include the hydrates thereof.

The compound of formula (I) may be modified to provide pharmaceutically acceptable derivatives thereof at any of the functional groups in the compound. Examples of such derivatives are described in: Drugs of Today, Volume 19, Number 9, 1983, pp 499–538; Topics in Chemistry, Chapter 31, pp 306–316; and in "Design of Prodrugs" by H. Bundgaard, Elsevier, 1985, Chapter 1 (the disclosures in which documents are incorporated herein by reference) and include: esters, carbonate esters, hemi-esters, phosphate esters, nitro esters, sulfate esters, sulfoxides, amides, sulphonamides, carbamates, azo-compounds, phosphamides, glycosides, ethers, acetals and ketals.

The invention encompasses all isomers of the compound of formula (I) and pharmaceutically acceptable salts, solvates or derivatives thereof, including all geometric, tautomeric and optical forms, and mixtures thereof (e.g. racemic mixtures).

Separation of diastereoisomers may be achieved by conventional techniques, e.g. by fractional crystallisation, chromatography or high performance liquid chromatography (HPLC) of a stereoisomeric mixture of compounds. An individual enantiomer of a compound may also be prepared from a corresponding optically pure intermediate or by resolution, such as by HPLC of the corresponding racemate using a suitable chiral support, or by fractional crystallisation of the diastereoisomeric salts formed by reaction of the corresponding racemate with a suitable optically active acid or base, as appropriate.

The compound of formula (I) and pharmaceutically acceptable salts, solvates or derivatives thereof may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behaviour, and melting point of the compound are used to distinguish polymorphs.

Compounds of formula (I), pharmaceutically acceptable salts, solvates and derivatives thereof, isomers thereof, and polymorphs thereof, are hereinafter referred to as the compounds of the invention.

Preferred compounds of the invention are the compounds of formula (I) and pharmaceutically acceptable salts and solvates thereof.

Preferably, $R^1$ is a five or six-membered, aromatic heterocyclic group containing (i) from 1 to 2 nitrogen heteroatom(s) or (ii) 1 nitrogen heteroatom and 1 oxygen or 1 sulphur heteroatom, said heterocyclic group being optionally substituted by halo, oxo, —CN, —OR$^5$, —OR$^{11}$, —NR$^5$R$^5$, —(C$_1$–C$_6$ alkylene)-NR$^5$R$^5$, R$^7$ or R$^{11}$.

Preferably, $R^1$ is a five or six-membered, aromatic heterocyclic group containing (i) from 1 to 2 nitrogen heteroatom(s) or (ii) 1 nitrogen heteroatom and 1 sulphur heteroatom, said heterocyclic group being optionally substituted by —OR$^{11}$, —NR$^5$R$^5$, R$^7$ or R$^{11}$. Preferably, $R^1$ is a five or six-membered, aromatic heterocyclic group containing (i) from 1 to 2 nitrogen heteroatom(s) or (ii) 1 nitrogen heteroatom and 1 sulphur heteroatom, said heterocyclic group being optionally substituted by $C_1$–$C_6$ alkyl, phenyl, phenoxy, $C_1$–$C_6$ alkoxyphenoxy or —NR$^5$R$^5$.

Preferably, $R^1$ is pyridinyl, pyrimidinyl, pyrazinyl or thiazolyl, each being optionally substituted by $C_1$–$C_2$ alkyl, phenyl, $C_1$–$C_2$ alkoxyphenoxy, —N(CH$_3$)$_2$, —N(CH$_2$CH$_3$)$_2$ or N(CH$_3$)(CH$_2$CH$_3$).

Preferably, $R^2$ is H, $C_1$–$C_6$ alkyl, $C_3$–$C_6$ alkenyl, phenyl, benzyl or $R^9$, said phenyl, benzyl or $C_1$–$C_6$ alkyl being optionally substituted by halo, —OR$^5$, —OR$^{10}$, —CN, —CO$_2$R$^7$, —OCONR$^5$R$^5$, —CONR$^5$R$^5$, —C(=NR$^5$)NR$^5$OR$^5$, —CONR$^5$NR$^5$R$^5$, —NR$^6$R$^6$, —NR$^5$R$^{10}$, —NR$^5$COR$^5$, —NR$^5$COR$^8$, —NR$^5$COR$^{10}$, —NR$^5$CO$_2$R$^5$, —NR$^5$CONR$^5$R$^5$, —SO$_2$NR$^5$R$^5$, —NR$^5$SO$_2$R$^5$, R$^8$ or R$^9$. Preferably, $R^2$ is $C_1$–$C_6$ alkyl, phenyl or benzyl, said $C_1$–$C_6$ alkyl being optionally substituted by halo, —OR$^5$, —OR$^{10}$ or —CN.

Preferably, $R^2$ is $C_1$–$C_3$ alkyl or benzyl, said $C_1$–$C_3$ alkyl being optionally substituted by —CN.

Preferably, $R^3$ is H, $C_1$–$C_6$ alkyl or $C_3$–$C_7$ cycloalkyl, said $C_1$–$C_6$ alkyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, R$^8$ or R$^9$.

Preferably, $R^3$ is H or $C_1$–$C_6$ alkyl.
Preferably, $R^3$ is H or $C_1$–$C_4$ alkyl.
Preferably, $R^3$ is methyl or ethyl.
Preferably, $R^4$ is phenyl optionally substituted by R$^8$, halo, —CN, $C_1$–$C_6$ alkyl, $C_1$–$C_6$ haloalkyl, $C_3$–$C_7$ cycloalkyl or $C_1$–$C_6$ alkoxy.

Preferably, $R^4$ is phenyl substituted by R$^8$, halo, —CN, $C_1$–$C_6$ alkyl, or $C_1$–$C_6$ alkoxy.

Preferably, $R^4$ is phenyl substituted by —CN.
Preferably, $R^4$ is 3,5-dicyanophenyl.
Preferably, $R^8$ is pyrrolyl, imidazolyl, pyrazolyl, 1,2,3-triazolyl, 1,2,4-triazolyl, tetrazolyl, oxazolyl, isoxazolyl, thiazolyl, isothiazolyl, 1,2,4-oxadiazolyl, 1,3,4-oxadiazolyl, furanyl, thienyl, pyridinyl, pyridazinyl, pyrimidinyl or pyrazinyl, each being optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, fluoro(C$_1$–C$_6$)alkyl or C$_3$–C$_7$ cycloalkyl.

Preferably, R$^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, fluoro(C$_1$–C$_6$)alkyl or C$_3$–C$_7$ cycloalkyl.

Preferably, R$^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by —OR$^5$, —NR$^5$R$^5$ or C$_1$–C$_6$ alkyl.

Preferably, R$^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by —OH, —NH$_2$ or methyl.

Preferably, R$^9$ is azetidinyl, tetrahydropyrrolyl, piperidinyl, azepinyl, oxetanyl, tetrahydrofuranyl, tetrahydropyranyl, oxepinyl, morpholinyl, piperazinyl or diazepinyl, each being optionally substituted by oxo, C$_1$–C$_6$ alkyl, C$_3$–C$_7$ cycloalkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN.

Preferably, R$^9$ is azetidinyl, piperidinyl, tetrahydrofuranyl, piperazinyl or morpholinyl, each being optionally substituted by oxo, C$_1$–C$_6$ alkyl, C$_3$–C$_7$ cycloalkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$or —CN.

Preferably, R$^9$ is azetidinyl, piperidinyl, tetrahydrofuranyl, piperazinyl or morpholinyl, each being optionally substituted by C$_1$–C$_6$ alkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by —OR$^5$ or —NR$^5$COR$^5$.

Preferably, R$^9$ is azetidinyl, piperidinyl, tetrahydrofuranyl, piperazinyl or morpholinyl, each being optionally substituted by —CH$_3$, —SO$_2$CH$_3$, —CONH$_2$, —COOCH$_3$, —COCH$_2$OCH$_3$ or —COCH$_3$ and optionally substituted on a carbon atom which is not adjacent to a heteroatom by —OCH$_3$ or —NHCOCH$_3$.

Preferably, R$^{10}$ is C$_1$–C$_4$ alkyl substituted by R$^8$, R$^9$, —OR$^5$, —CONR$^5$R$^5$, —NR$^5$COR$^5$ or —NR$^5$R$^5$.

Preferably, R$^{10}$ is C$_1$–C$_4$ alkyl substituted by R$^9$, —OR$^5$, —NR$^5$COR$^5$ or —NR$^5$R$^5$.

Preferably, R$^{10}$ is C$_1$–C$_2$ alkyl substituted by tetrahydrofuranyl, —OCH$_3$, —NHCOCH$_3$ or —NH$_2$.

Preferably, R$^{11}$ is phenyl substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, halo(C$_1$–C$_6$)alkyl or C$_3$–C$_7$ cycloalkyl.

Preferably, R$^{11}$ is phenyl substituted by halo, —CN, —CONR$^5$R$^5$, —SO$_2$NR$^5$R$^5$ or —OR$^5$.

Preferably, R$^{11}$ is phenyl substituted by —OR$^5$.

Preferably, R$^{11}$ is phenyl substituted by C$_1$–C$_2$ alkoxy.

Preferred groups of compounds according to the invention include all combinations of the preferred definitions for individual substituents given above.

Preferred compounds of the invention are: 5-[3-Ethyl-1-methyl-5-(pyridin-2-yloxy)-1H-pyrazol-4-yloxy]-isophthalonitrile; the compound of Example 6; and its pharmaceutically acceptable salts, solvates or derivatives.

The compounds of the invention may have advantages over those of the prior art with regard to a number of useful properties or combination thereof, such as potency, duration of action, pharmacokinetics, spectrum of activity, side effect profile, solubility, chemical stability, and so on.

The compounds of the invention may be prepared by any method known in the art for the preparation of compounds of analogous structure. The compounds of the invention can be prepared by the procedures described in the methods below, or by the specific methods described in the Examples, or by similar methods to either. The invention also encompasses any one or more of these processes for preparing the compounds of the invention, in addition to any novel intermediates used therein.

In the following methods, R$^1$, R$^2$, R$^3$ and R$^4$ are as previously defined for a compound of formula (I), unless otherwise stated, and R$^a$ is an alkyl group, such as a lower alkyl group (e.g. methyl).

Compounds of formula (I) may be prepared according to Scheme 1.

According to Scheme 1, compounds of formula (I) may be prepared by the reaction of a compound of formula (V) with an alcohol of formula (IV) under conventional conditions. Conveniently, the reaction is effected in the presence of a catalyst, such as a transition metal catalyst, preferably a palladium catalyst (e.g. 1,1'-bis(diphenylphosphino)ferrocenepalladium(II)chloride); a solvent, such as a polar aprotic solvent (e.g. N,N-dimethylformamide); at ambient to elevated temperature, such as around 50° C.; under an inert atmosphere, such as carbon monoxide; and at elevated pressure, such as around 345 kPa.

Compounds of formula (V) may be prepared from compounds of formula (III) by derivatising the hydroxy group therein to provide a leaving group (Lg). Conveniently, Lg is a reactive ester group, such as a sulphonic ester group, (e.g. trifluoromethanesulphonate). Conveniently, the reaction is effected in the presence of a derivatising agent, such as a sulphonic amide, (e.g. phenyltriflamide); a base, such as a trialkylamine base (e.g. triethylamine); a solvent such, such as a halogenated alkane (e.g. dichloromethane); and at ambient to elevated temperature, such as ambient temperature.

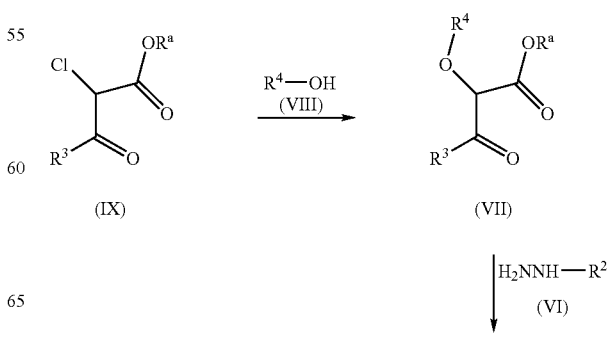

Scheme 1

-continued

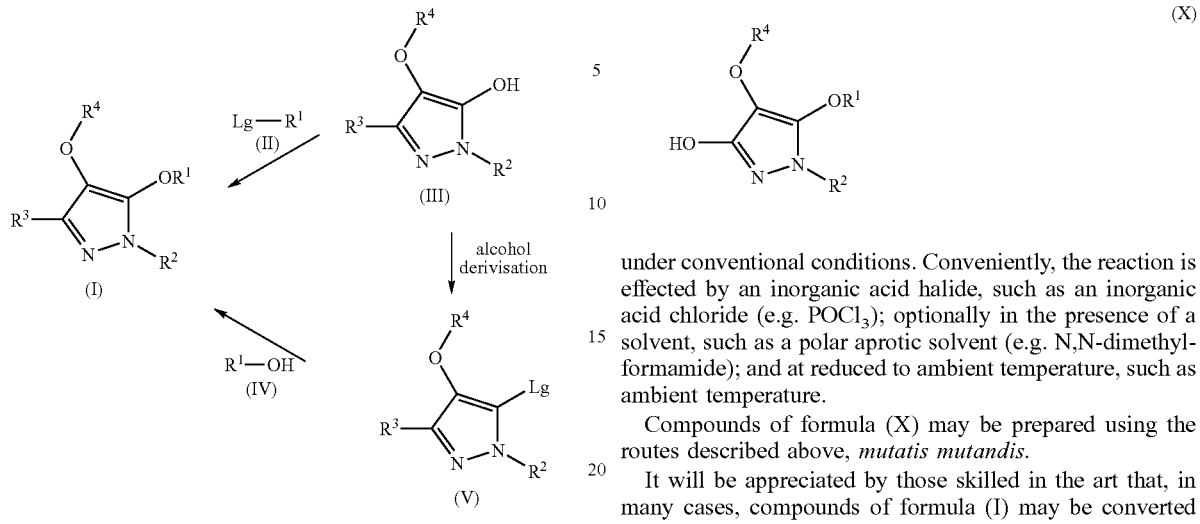

Compounds of formula (III) may be prepared by the reaction of a compound of formula (VII) with a hydrazine of formula (VI), or a salt or hydrate thereof. Conveniently, the reaction is effected a solvent, such as a protic solvent (e.g. acetic acid); at ambient to elevated temperature, such as ambient temperature; and optionally in the presence of an acid (e.g. acetic acid) or a base, such as a tertiary amine (e.g. triethylamine).

Compounds of formula (VII) may be prepared by the reaction of a compound of formula (IX) with an alcohol of formula (VIII). Conveniently, the reaction is effected in the presence of a solvent, such as a polar solvent (e.g. acetone); a base, such as an inorganic base, preferably a metal carbonate (e.g. potassium or caesium carbonate); optionally, a nucleophilic catalyst, such as sodium iodide or tetrabutylammonium iodide; and at ambient to elevated temperature, such as elevated temperature (e.g. under reflux).

Chloroketoesters of formula (IX) are either commercially available, known in the literature, or may be prepared by conventional methods (e.g. the chlorination of the corresponding ketoesters, for instance using sulphonyl chloride).

According to Scheme 1, compounds of formula (I) may also be prepared by the reaction of an alcohol of formula (III) with a compound of formula (II) under conventional conditions. Conveniently, the reaction is effected in the presence of a base, such as an inorganic base, preferably a metal carbonate (e.g. potassium carbonate); optionally a solvent, such as a polar aprotic solvent (e.g. N,N-dimethylacetamide); optionally a catalyst, such as a copper(I) catalyst; and at ambient to elevated temperature, such as elevated temperature (e.g. under reflux).

Alternatively, compounds of formula (I) may be prepared from compounds of formula (III) by reaction with an alcohol of formula (IV) under dehydrating conditions, such as afforded by the Mitsunobu reaction. Conveniently, the reaction is effected in the presence of diethylazodicarboxylate, triphenylphosphine, a solvent, such as an ether, (e.g. tetrahydrofuran); and at reduced to ambient temperature, such 0° C.

Compounds of formula (I) in which $R^3$ is halo can be prepared from a compound of formula (X)

under conventional conditions. Conveniently, the reaction is effected by an inorganic acid halide, such as an inorganic acid chloride (e.g. $POCl_3$); optionally in the presence of a solvent, such as a polar aprotic solvent (e.g. N,N-dimethylformamide); and at reduced to ambient temperature, such as ambient temperature.

Compounds of formula (X) may be prepared using the routes described above, *mutatis mutandis*.

It will be appreciated by those skilled in the art that, in many cases, compounds of formula (I) may be converted into other compounds of formula (I) by functional group transformations, including for example the following interconversions.

Compounds of formula (I) in which $R^2$ is optionally substituted $C_1$–$C_6$ alkyl may be prepared from compounds of formula (I) in $R^2$ is H by reaction with an alkylating agent. Suitable alkylating agents include bromoacetonitrile, ethyl 4-Chloroacetoacetate, methyl bromoacetate and chloroethylamine hydrochloride. Conveniently, alkylation is effected in the presence of a suitable solvent, such as an alcohol (e.g. ethanol) or a polar aprotic solvent (e.g. N,N-dimethylformamide); a base, such as a metal hydride (e.g. sodium hydride) or metal alkoxide (e.g. sodium ethoxide); and at ambient to elevated temperature, such as under reflux.

Compounds of formula (I) in which $R^2$ or $R^3$ contains a hydroxy group may be prepared from the corresponding compound of formula (I) in which $R^2$ or $R^3$ contains an ester group by reduction. Conveniently, the reduction is effected by a metal hydride agent, such as lithium aluminium hydride; in a solvent, such as an ether (e.g. diethyl ether); and at reduced temperature, such as from –78° C. to 0° C.

Compounds of formula (I) in which $R^2$ or $R^3$ are substituted by a heterocycle of formula $R^8$ and $R^9$ may be prepared by standard heterocycle-forming reactions well known to the skilled man (see, for example, Advanced Organic Chemistry, 3rd Edition, by Gerry March or Comprehensive Heterocyclic Chemistry, A. R. Katritzky, C. W. Rees, E. F. V. Scriven, Volumes 1–11).

Compounds of formula (I) in which $R^3$ is —$CO_2H$ may be prepared by hydrolysis of a corresponding compound of formula (I) in which $R^3$ is —$CO_2R^5$. Conveniently, the reaction is effected in the presence of a solvent, such as an alcohol (e.g. aqueous ethanol), or an ether (e.g. aqueous 1,4-dioxan); and in the presence of a base, such as a metal hydroxide (e.g. sodium hydroxide). The skilled artisan will appreciate that such an acid may be converted into a primary amide by reaction with ammonia and a suitable coupling agent, such as a carbodiimide, e.g. dicyclohexylcarbodiimide, and that such a primary amide may then be converted into a nitrile by dehydration with a suitable dehydrating agent, such as phosphoryl chloride.

Compounds of formula (I) in which $R^3$ is $C_1$–$C_6$ alkyl may be converted into the compounds of formula (I) in which $R^3$ is $C_1$–$C_6$ alkyl substituted by halo (such as bromo), by halogenation, using a suitable halogenating agent. Conveniently the reaction is effected in the presence of a solvent, such as a haloalkane (e.g. dichloromethane) and at ambient temperature. Suitable halogenating agents include halogens (e.g. bromine) or N-halosuccinimides (e.g. N-bromsuccinimide).

Compounds of formula (I) containing an —OH, —NH— or —NH$_2$ group may be prepared by the deprotection of the corresponding compound bearing an —OP$^1$, —NP$^1$— or —NHP$^1$ group, respectively, wherein the group P$^1$ is a suitable protecting group. Examples of suitable protecting groups will be apparent to the skilled person; see, for instance, 'Protecting groups in Organic Synthesis (Second Edition)' by Theodora W. Green and Peter G. M. Wuts, 1991, John Wiley and Sons. Such compounds bearing an —OP$^1$, —NP$^1$— or —NHP$^1$ group may be prepared using the routes described above, *mutatis mutandis*.

Compounds of formulae (II), (IV) and (VI) and (VII) are either commercially available, known in the literature or easily prepared by methods well known to those skilled in the art, such as those described in the Preparations hereinafter.

Compounds of formulae (III), (V) or (X) are key intermediates and form a further aspect of the invention.

The compounds of the invention can be administered alone, but will generally be administered in admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the invention may also be administered as fast-dispersing or fast-dissolving dosage forms or in the form of a high energy dispersion or as coated particles. Suitable formulations of the compounds of the invention may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

General Example

A formulation of the tablet could typically contain from 0.01 mg to 500 mg of active compound whilst tablet fill weights may range from 50 mg to 1000 mg. An example of a formulation for a 10 mg tablet is illustrated below:

| Ingredient | % w/w |
| --- | --- |
| Compound of the invention | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention will usually be from 0.01 to 30 mg/kg, preferably from 0.01 to 5 mg/kg (in single or divided doses).

Thus tablets or capsules of the compound of the invention may contain from 1 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will appreciate that, in the treatment of certain conditions the compounds of the invention may be taken as a single dose as needed or desired.

The compounds of invention can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the pulmonary or rectal routes.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO91/11172, WO94/02518 and WO98/55148.

It is to be appreciated that all references herein to treatment include curative, palliative and prophylactic treatment.

Oral Administration is Preferred.

Included within the scope of the invention are embodiments comprising the co-administration of a compound of the invention with one or more additional therapeutic agents, and compositions containing a compound of the invention along with one or more additional therapeutic agents. Such a combination therapy is especially useful for the prevention and/or treatment of infection by HIV and related retroviruses which may evolve rapidly into strains resistant to any monotherapy. Alternatively, additional therapeutic agents may be desirable to treat diseases and conditions which result from or accompany the disease being treated with the compound of the invention. For example, in the treatment of an HIV or related retroviral infection, it may be desirable to additionally treat opportunistic infections, neoplasms and other conditions which occur as a result of the immuno-compromised state of the patient being treated.

Preferred combinations of the invention include simultaneous or sequential treatment with a compound of the invention and one or more:

(a) reverse transcriptase inhibitors such as abacavir, adefovir, didanosine, lamivudine, stavudine, zalcitabine and zidovudine;

(b) non-nucleoside reverse transcriptase inhibitors such as capavirine, delavirdine, efavirenz, and nevirapine;

(c) HIV protease inhibitors such as indinivir, nelfinavir, ritonavir, and saquinavir;

(d) $CCR^5$ antagonists such as TAK-779 or UK-427,857;

(e) $CXCR^4$ antagonists such as AMD-3100;

(f) integrase inhibitors, such as L-870,810 or S-1360;

(g) inhibitors of viral fusion such as T-20;

(h) investigational drugs such as trizivir, KNI-272, amprenavir, GW-33908, FTC, PMPA, MKC-442, MSC-204, MSH-372, DMP450, PNU-140690, ABT-378, KNI-764, DPC-083, TMC-120 or TMC-125;

(i) antifungal agents, such as fluconazole, itraconazole or voriconazole; or (j) antibacterial agents, such as azithromycin.

The activity of the compounds of the invention as reverse transcriptase inhibitors may be measured using the following assay.

Inhibition of HIV-1 Reverse Transcriptase Enzyme

Using purified recombinant HIV-1 reverse transcriptase (RT, EC, 2.7.7.49) obtained by expression in Escherichia Coli, a 96-well plate assay system is established for assaying a large number of samples using either the Poly(rA)-oligo (dT) Reverse Transcriptase [3H]-SPA enzyme assay system (Amersham NK9020) or the [3H]-flashplate enzyme assay system (NEN-SMP 103) and following the manufacturer's recommendations. The compounds are dissolved in 100% DMSO and diluted with the appropriate buffer to a 5% final DMSO concentration. The inhibitory activity is expressed in percent inhibition relative to DMSO control. The concentration at which compound inhibits reverse transcriptase by 50% is expressed as the $IC_{50}$ of the compound.

The compound of Examples 1 and 6, when tested according to the above procedure, had an $IC_{50}$ values of, respectively, 5400 and 391 nanomolar.

Thus the invention provides:

(i) a compound of formula (I) or a pharmaceutically acceptable salt, solvate or derivative thereof;

(ii) a process for the preparation of a compound of formula (I) or a pharmaceutically acceptable salt, solvate or derivative thereof;

(iii) a pharmaceutical composition including a compound of formula (I) or a pharmaceutically acceptable salt, solvate or derivative thereof, together with a pharmaceutically acceptable excipient, diluent or carrier;

(iv) a compound of formula (I) or a pharmaceutically acceptable salt, solvate or composition thereof, for use as a medicament;

(v) a compound of formula (I) or a pharmaceutically acceptable salt, solvate or composition thereof, for use as a reverse transcriptase inhibitor or modulator;

(vi) a compound of formula (I) or a pharmaceutically acceptable salt, solvate or composition thereof, for use in the treatment of an HIV or genetically-related retroviral infection, or a resulting acquired immune deficiency syndrome (AIDS);

(vii) a use of the compound of formula (I) or of a pharmaceutically acceptable salt, solvate or composition thereof, for the manufacture of a medicament having reverse transcriptase inhibitory or modulating activity;

(viii) the use of a compound of formula (I) or of a pharmaceutically acceptable salt, solvate or composition thereof, for the manufacture of a medicament for the treatment of an HIV or genetically-related retroviral infection, or a resulting acquired immune deficiency syndrome (AIDS);

(ix) a method of treating an HIV or a genetically-related retroviral infection, or a resulting acquired immune deficiency syndrome (AIDS), comprising administering an effective amount of a compound of formula (I) or a pharmaceutically acceptable salt, solvate or composition thereof; and (xi) certain novel intermediates disclosed herein.

The following Examples illustrate the preparation of the compounds of formula (I). The synthesis of certain intermediates used therein are described in the Preparations section that follows the Examples.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used: HRMS, high resolution mass spectrometry; hplc, high performance liquid chromatography; nOe, nuclear Overhauser effect; m.p., melting point; CDCl$_3$, deuterochloroform; D$_6$-DMSO, deuterodimethylsulphoxide; CD$_3$OD, deuteromethanol. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

EXAMPLE 1

5-[3-Ethyl-1-methyl-5-(pyridin-2-yloxy)-1H-pyrazol4-yloxy]-isophthalonitrile

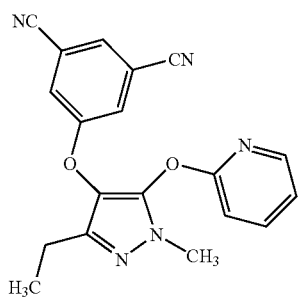

The pyrazole of Preparation 5 (10 mg, 0.37 mmol) and 2-chloropyridine (55 mg, 0.49 mmol) were mixed and heated to 145° C. for 1.5 hours. The mixture was cooled to room temperature and partitioned between ethyl acetate (10 ml) and water (10 ml). The aqueous solution was extracted with ethyl acetate (2×10 ml). The combined organic solutions were evaporated under reduced pressure and the residue was purified by chromatography on silica gel using methanol in dichloromethane (1:99) to give the title compound as a yellow solid (30 mg).

$^1$H NMR (400 MHz, CD$_3$OD): δ 1.18 (m, 3H), 2.49 (m, 2H), 3.60 (s, 3H), 7.00 (m, 1H), 7.15 (m, 1H), 7.6 (s, 2H), 7.72 (m, 1H), 7.80 (m, 1H), 8.12 (m, 1H). LRMS (APCl): m/z [M+H]$^+$ 346

EXAMPLES 2–10

The compounds of Table 1 of the general formula:

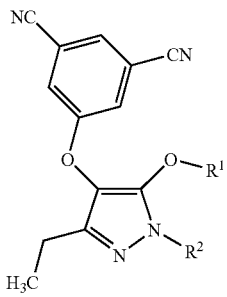

were prepared by a method analogous to that of Example 1 using the appropriate pyrazole and aryl halide.

TABLE 1

| Example No. | R$^1$ | R$^2$ |
|---|---|---|
| 2 | pyrimidin-2-yl | CH$_3$ |
| 3 | 5-methylpyrimidin-2-yl | CH$_3$ |
| 4$^A$ | 5-phenylpyrimidin-2-yl | CH$_3$ |
| 5 | 4-(dimethylamino)pyrimidin-2-yl | CH$_3$ |
| 6$^B$ | 5-(4-methoxyphenoxy)pyrimidin-2-yl | CH$_3$ |
| 7 | pyrazin-2-yl | CH$_3$ |
| 8 | thiazol-2-yl | CH$_3$ |

TABLE 1-continued

| Example No. | R¹ | R² |
|---|---|---|
| 9 | pyrimidin-2-yl | CH₂CH₂CN |
| 10 | pyrimidin-2-yl | CH₂-phenyl |

<sup>A</sup>starting pyrimidine, see J. Het. Chem, 1980, 17(7) 1479.
<sup>B</sup>starting pyrimidine supplied by Peakdale Fine Chemicals

EXAMPLE 2

$^1$H NMR (400 MHz, DMSO-d$_6$): δ 1.10 (m, 3H), 2.40 (m, 2H), 3.6 (s, 3H), 7.38 (m, 1H), 7.8 (s, 2H), 8.05 (s, 1H), 8.62 (m, 2H). LRMS (APCl): m/z [M+H]$^+$ 347

EXAMPLE 3

$^1$H NMR (400 MHz, CDCl$_3$): δ 1.26 (m, 6H), 2.48 (m, 2H), 2.64 (m, 2H), 3.70 (s, 3H), 7.50 (m, 3H), 8.38 (m, 2H) LRMS (APCl): m/z [M+H]$^+$ 375.

EXAMPLE 4

$^1$H NMR (400 MHz, CDCl$_3$): δ 1.20 (m, 3H), 2.48 (m, 2H), 3.75 (s, 3H), 7.50 (m, 8H), 8.70 (m, 2H). LRMS (APCl): m/z [M+H]$^+$ 423

EXAMPLE 5

$^1$H NMR (400 MHz, CDCl$_3$): δ 1.20 (m, 3H), 2.49 (m, 2H), 3.15 (m, 6H), 3.70 (s, 3H), 6.23 (m, 1H), 7.45 (m, 2H), 8.00 (m, 2H). LRMS (APCl): m/z [M+H]$^+$ 390

EXAMPLE 6

$^1$H NMR (400 MHz, CDCl$_3$): δ 1.20 (m, 3H), 2.48 (m, 2H), 3.82 (s, 3H), 3.85 (s, 3H), 6.95 (m, 4H), 7.42 (s, 2H), 7.52 (s, 1H), 8.20 (s, 2H). LRMS (APCl): m/z [M+H]$^+$ 469

EXAMPLE 7

$^1$H NMR (400 MHz, CDCl$_3$): δ 1.20 (m, 3H), 2.48 (m, 2H), 3.70 (s, 3H), 7.42 (s, 2H), 7.50 (s, 1H), 8.00 (s, 1H), 8.38 (s, 1H), 8.42 (s, 1H). LRMS (APCl): m/z [M+H]$^+$ 347

EXAMPLE 8

$^1$H NMR (400 MHz, CDCl$_3$): δ 1.20 (m, 3H), 2.48 (m, 2H), 3.80 (s, 3H), 6.80 (m, 1H), 7.10 (m, 1H), 7.42 (s, 2H), 7.50 (s, 1H). LRMS (APCl): m/z [M+H]$^+$ 352

EXAMPLE 9

$^1$H NMR (400 MHz, DMSO0-d$_6$): δ 1.10 (m, 3H), 2.47 (m, 2H), 3.0 (m, 2H), 4.20 (m, 2H), 7.38 (m, 1H), 7.5 (s, 2H), 8.05 (s, 1 H), 8.60 (m, 2H). LRMS (APCl): m/z [M+H]$^+$ 386

EXAMPLE 10

$^1$H NMR (400 MHz, CDCl$_3$): δ 1.20 (m, 3H), 2.54 (m, 2H), 5.2 (s, 2H), 7.00 (m, 1H), 7.15–7.25 (m, 5H), 7.5 (s, 3H), 8.4 (m, 2H). LRMS (APCl): m/z [M+H]$^+$ 423

EXAMPLE 11

5-[3-Ethyl-1-(2-hydroxy-ethyl)-5-(pyridin-2-yloxy)-1H-pyrazol-4-yloxy]-isophthalonitrile

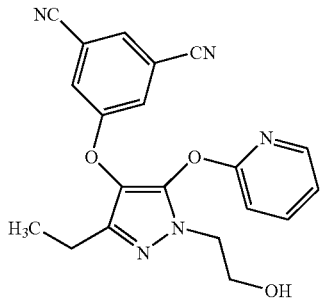

Tetrabutylammonium fluoride (1M in tetrahydrofuran, 72 μl, 0.07 mmol) was added to a solution of the silyl ether of Preparation 10 (32 mg, 0.07 mmol) in tetrahydrofuran (3 ml) and the mixture was stirred for 1.5 hours. A further quantity of tetrabutylammonium fluoride (1M in tetrahydrofuran, 33 μl, 0.03 mmol) was added and the mixture was stirred for a further 45 minutes. Brine and dichloromethane were added and the layers were separated. The organic layer was dried over magnesium sulphate and evaporated under reduced pressure. The residue was purified by chromatography on silica gel using methanol in dichloromethane (gradient from 2:98 to 3.5:96.5) to give the title compound as a yellow oil (21 mg).

$^1$H NMR (400 MHz, CDCl$_3$): δ 1.18 (m, 3H), 2.49 (m, 2H), 4.07 (m, 4H), 6.90 (m, 1H), 7.10 (m, 1H), 7.45 (m, 3H), 7.60 (m, 1H), 8.10 (m, 1H). LRMS (APCl): m/z [M+H]$^+$ 376.

Preparation 1

1.3-Dibromo-5-methoxybenzene

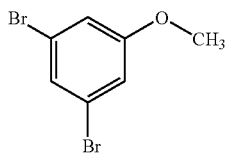

Sodium methoxide (4.5M solution in methanol, 8.80 ml, 41.0 mmol) was added dropwise to a stirred solution of 3,5-dibromofluorobenzene (5.00 g, 19.0 mmol, Aldrich) in N,N-dimethylformamide (95 ml) at 0° C. under a nitrogen atmosphere. The reaction was warmed to room temperature, stirred for 1 hour and then evaporated under reduced pressure. The residue was dissolved in diethyl ether and was washed with water (3×300 ml) and brine (300 ml), dried over magnesium sulphate, filtered and concentrated under reduced pressure to give the title compound as a white solid (5.13 g).

$^1$H-NMR (300 MHz, CDCl$_3$): δ 3.79 (s, 3H), 7.00 (s, 2H), 7.26 (s, 1H). LRMS: m/z TS+266 [M+H]$^+$

Preparation 2

3.5-Dicyanomethoxybenzene

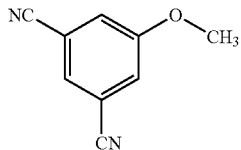

Tris(dibenzylideneacetone)dipalladium(0) (6.53 g, 7.15 mmol) was added in one portion to a stirred solution of the bromide of Preparation 1 (38.0 g, 143 mmol), 1,1'-bis(diphenylphosphino)ferrocene (9.3 g, 16.8 mmol) and zinc cyanide (20.0 g, 172 mmol) in N,N-dimethylformamide (300 ml) at room temperature under nitrogen. The reaction was heated at 100° C. for 14 hours and cooled to room temperature. Water (1500 ml) was added and the mixture was extracted with ethyl acetate (3×500 ml). The combined organics were filtered and the filtrate was washed with water (500 ml), dried over magnesium sulphate, filtered and concentrated under reduced pressure. The resulting solid was triturated with toluene (1000 ml) to provide the title compound (18.0 g) as a tan solid.

$^1$H-NMR (300MHz, CDCl$_3$): δ=3.83 (3H, s), 7.31 (2H, s), 7.48 (1H, s).

Preparation 3

3.5-Dicyanohydroxybenzene

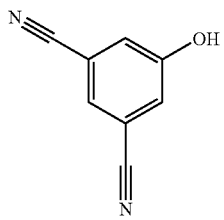

The ether of Preparation 2 (9.60 g, 60.7 mmol) was added portionwise to a stirred suspension of aluminium trichloride (32.4 g, 243 mmol) in dichloromethane (250 ml) at 0° C. under a nitrogen atmosphere. The suspension was stirred at 45° C. for 6 days, then cooled to room temperature and poured onto ice (450 ml). Concentrated hydrochloric acid (450 ml) was added dropwise and the resulting suspension was stirred for 10 minutes at room temperature. The solid formed was isolated by filtration, washed with water and dried over phosphorus pentoxide to give the title compound as a tan solid (7.83 g).

$^1$H-NMR (400 MHz, CDCl$_3$): δ 7.36 (m, 2H), 7.56 (m, 1H).

Preparation 4

2-(3,5-Dicyano-phenoxy)-3-oxo-pentanoic acid methyl ester

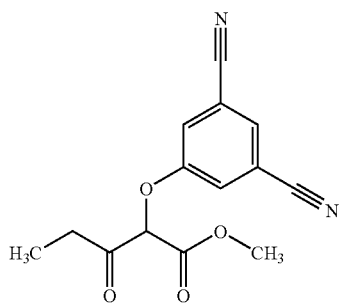

A solution of 2-chloro-3-oxo-pentanoic acid methyl ester (20 g, 121.5 mmol) in acetone (100 ml) was added to the phenol from Preparation 3 (17.5 g, 121.5 mmol) and caesium carbonate (43.5 g, 133.6 mmol) in acetone (400 ml) under a nitrogen atmosphere. The mixture was stirred at room temperature for 15 minutes and then heated under reflux for 2.5 hours. Water was added and the solvent was evaporated under reduced pressure. The residual aqueous solution was extracted with dichloromethane (3×300 ml) and the combined organic layers were dried over magnesium sulphate and evaporated under reduced pressure. The residual orange oil was pre-adsorbed onto silica gel and then purified by chromatography on silica gel using ethyl acetate in pentane (gradient from 20:80 to 80:20) to give the title compound as a yellow solid (27 g).

M.p. 93–95° C. Found; C, 61.57; H, 4.54; N, 10.06; C$_{14}$H$_{12}$N$_2$O$_4$ requires C, 61.76; H, 4.44; N, 10.29%.

Preparation 5

5-(3-Ethyl-1-methyl-5-oxo-4.5-dihydro-1H-pyrazol-4-yloxy)-isophthalonitrile

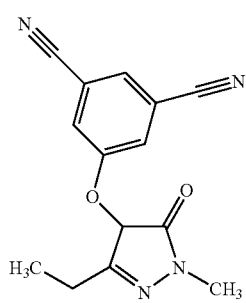

The ester from Preparation 4 (4 g, 14.7 mmol) was dissolved in acetic acid (50 ml) and methyl hydrazine (0.87 ml, 16.2 mmol) was added. The mixture was stirred at room temperature under a nitrogen atmosphere for 3 hours and the solvent was evaporated under reduced pressure. The residue was triturated with diethyl ether to give the title compound as a pink solid (2.75 g).

M.p. 235-dec LRMS: m/z ES+269 [M+H]$^+$

Preparation 6

5-[1-(2-Cyano-ethyl)-3-ethyl-5-oxo-4,5-dihydro-1H-pyrazol-4-yloxy]-isophthalonitrile

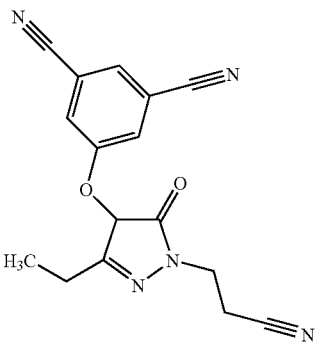

The title compound was obtained from the ester of preparation 4 and 3-hydrazino-propionitrile in 57% yield following a procedure analogous to that described in Preparation 5.

M.p. 203.5–204.5° C. APCl MS m/z 308 [M+H]$^+$

Preparation 7

5-[3-Ethyl-1-(2-hydroxy-ethyl)-5-oxo-4,5-dihydro-1H-pyrazol4-yloxy]-isophthalonitrile

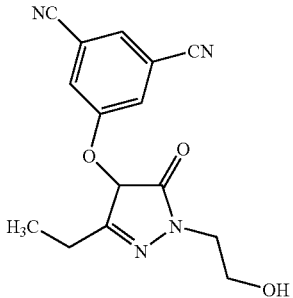

The title compound was obtained in 73% yield from the ester of preparation 4 and 2-hydrazino-ethanol following a procedure analogous to that described in Preparation 5.

M.p. 203.5–204.5° C. APCl MS m/z 297 [M–H]$^-$

Preparation 8

5-(1-Benzyl-3-ethyl-5-oxo-4,5-dihydro-1H-pyrazol-4-yloxy)-isophthalonitrile

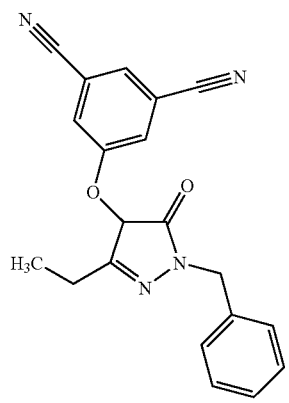

The title compound was obtained from the ester of preparation 4 and benzyl hydrazine in 52% yield following a procedure analogous to that described in Preparation 5.

APCl MS m/z 345 [M+H]$^+$

Preparation 9

5-{1-[2-(tert-Butyl-dimethyl-silanyloxy)-ethyl]-3-ethyl-5-oxo-4,5-dihydro-1H-pyrazol-4-yloxy}-isophthalonitrile

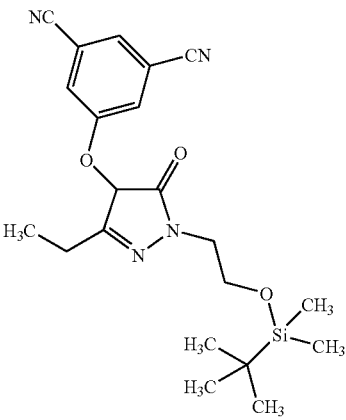

tert-Butyl-dimethyl-silyl chloride (2.4 g, 16.1 mmol) was added to a solution of the alcohol of preparation 7 (4.0 g, 13.4 mmol) in N,N-dimethylformamide (20 ml) and triethylamine (5.6 ml, 40.3 mmol). The mixture was stirred at room temperature under a nitrogen atmosphere for 3 hours and then was partitioned between ethyl acetate and water. The organic layer was washed with brine (2×100 ml) dried over magnesium sulphate and evaporated under reduced pressure. The residue was purified by chromatography on silica gel using dichloromethane as eluant to give the title compound (3.6 g).

M.p. 203.5–204.5° C. APCl MS m/z 413 [M+H]$^+$

Preparation 10

5-[1-[2-(tert-Butyl-dimethyl-silanyloxy)-ethyl]-3-ethyl-5-(pyridin-2-yloxy)-1H-pyrazol-4-yloxy]-isophthalonitrile

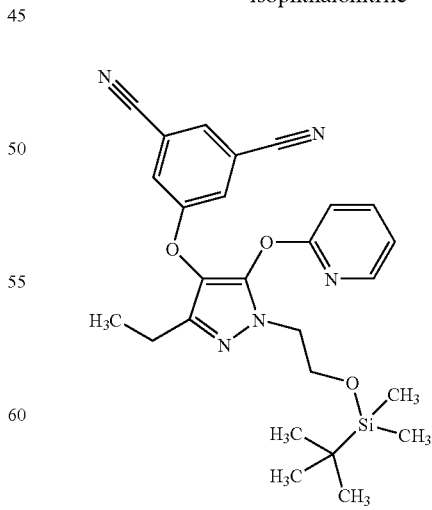

A mixture of the pyrazole of preparation 9 (150 mg, 0.36 mmol) and 2-chloropyridine (54 mg, 0.47 mmol) was heated to 150° C. for 2 hours and then was partitioned between ethyl acetate and water. The organic layer was evaporated under reduced pressure and the residue was purified by chromatography on silica gel using methanol in dichloromethane as eluant (2:98) to give the title compound (32 mg).

LCMS: m/z ES$^+$ 512 [M+Na]$^+$

The invention claimed is:

1. A compound of formula (I)

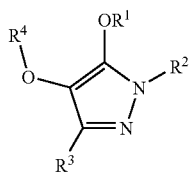

(I)

or a pharmaceutically acceptable salt, solvate or derivative thereof, wherein:

$R^1$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, OR$^{11}$, —NR$^5$R$^5$, —(C$_1$–C$_6$ alkylene)-NR$^5$R$^5$, R$^7$ or R$^{11}$;

$R^2$ is H, C$_1$–C$_6$ alkyl, C$_3$–C$_6$ alkenyl, C$_3$–C$_6$ alkynyl, C$_3$–C$_7$ cycloalkyl, C$_3$–C$_7$ cycloalkenyl, phenyl, benzyl, R$^8$ or R$^9$, said C$_1$–C$_6$ alkyl, C$_3$–C$_7$ cycloalkyl, phenyl and benzyl being optionally substituted by halo, —OR$^5$, —OR$^{10}$, —CN, —CO$_2$R$^7$, —OCONR$^5$R$^5$, —CONR$^5$R$^5$, —C(=NR$^5$)NR$^5$OR$^5$, —CONR$^5$NR$^5$R$^5$, —NR$^6$R$^6$, —NR$^5$R$^{10}$, —NR$^5$COR$^5$, —NR$^5$COR$^8$, —NR$^5$COR$^{10}$, —NR$^5$CO$_2$R$^5$, —NR$^5$CONR$^5$R$^5$, —SO$_2$NR$^5$R$^5$, —NR$^5$SO$_2$R$^5$, —NR$^5$SO$_2$NR$^5$R$^5$, R$^8$ or R$^9$;

$R^3$ is H, C$_1$–C$_6$ alkyl, C$_3$–C$_7$ cycloalkyl, phenyl, benzyl, halo, —CN, —OR$^7$, —CO$_2$R$^5$, —CONR$^5$R$^5$, R$^8$ or R$^9$, said C$_1$–C$_6$ alkyl, C$_3$–C$_7$ cycloalkyl, phenyl and benzyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, R$^8$ or R$^9$;

$R^4$ is phenyl substituted by —CN;

each $R^5$ is independently either H, C$_1$–C$_6$ alkyl or C$_3$–C$_7$ cycloalkyl;

each $R^6$ is independently either H, C$_1$–C$_6$ alkyl or C$_3$–C$_7$ cycloalkyl;

$R^7$ is C$_1$–C$_6$ alkyl or C$_3$–C$_7$ cycloalkyl;

$R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, fluoro(C$_1$–C$_6$)alkyl or C$_3$–C$_7$ cycloalkyl;

$R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, C$_1$–C$_6$ alkyl, C$_3$–C$_7$ cycloalkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN;

$R^{10}$ is C$_1$–C$_6$ alkyl substituted by R$^8$, R$^9$, —OR$^5$, —CONR$^5$R$^5$, —NR$^5$COR$^5$ or —NR$^5$R$^5$;

$R^{11}$ is phenyl optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, halo(C$_1$–C$_6$)alkyl or C$_3$–C$_7$ cycloalkyl; and x is 0, 1 or 2.

2. A pharmaceutical composition comprising a compound according to claim 1 and one or more pharmaceutically acceptable excipients, diluents or carriers.

3. A pharmaceutical composition according to claim 2 comprising one or more additional therapeutic agents.

4. A compound of formula (III) or (X)

(III)

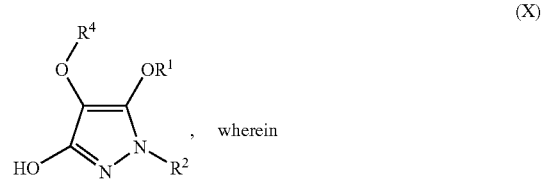

(X)

, wherein $R^1$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, OR$^{11}$, —NR$^5$R$^5$, —(C$_1$–C$_6$ alkylene)-NR$^5$R$^5$, R$^7$ or R$^{11}$;

$R^2$ is H, C$_1$–C$_6$ alkyl, C$_3$–C$_6$ alkenyl, C$_3$–C$_7$ alkynyl, C$_3$–C$_7$ cycloalkyl, C$_3$–C$_7$ cycloalkenyl, phenyl, benzyl, R$^8$ or R$^9$, said C$_1$–C$_6$ alkyl, C$_3$–C$_7$ cycloalkyl, phenyl and benzyl being optionally substituted by halo, —OR$^5$, OR$^{10}$, —CN, —CO$_2$R$^7$, —OCONR$^5$R$^5$, —OCNR$^5$R$^5$, —C(=NR$^5$)NR$^5$OR$^5$, —CON$^5$NR$^5$R$^5$, —NR$^6$R$^6$, —NR$^5$R$^{10}$, —NR$^5$COR$^5$, —NR$^5$COR$^8$, —NR$^5$COR$^{10}$, —NR$^5$CO$_2$R$^5$, —NR$^5$CONR$^5$R$^5$, —SO$_2$NR$^5$R$^5$, —NR$^5$SO$_2$R$^5$, —NR$^5$SO$_2$NR$^5$R$^5$, R$^8$ or R$^9$;

$R^3$ is H, C$_1$–C$_6$ alkyl, C$_3$–C$_7$ cycloalkyl, phenyl, benzyl, halo, —CN, —OR$^7$, —CO$_2$R$^5$, —CONR$^5$R$^5$, R$^8$ or R$^9$, said C$_1$–C$_6$ alkyl, C$_3$–C$_7$ cycloalkyl, phenyl and benzyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, R$^8$ or R$^9$;

$R^4$ is phenyl substituted by —CN;

each $R^5$ is independently either H, C$_1$–C$_6$ alkyl or C$_3$–C$_7$ cycloalkyl;

each $R^6$ is independently either H, $C_1$–$C_6$ alkyl or $C_3$–$C_7$ cycloalkyl;

$R^7$ is $C_1$–$C_6$ alkyl or $C_3$–$C_7$ cycloalkyl;

$R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, $C_1$–$C_6$ alkyl, fluoro(C$_1$–C$_6$)alkyl or $C_3$–$C_7$ cycloalkyl;

$R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, $C_1$–$C_6$ alkyl, $C_3$–$C_7$ cycloalkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN;

$R^{10}$ is $C_1$–$C_6$ alkyl substituted by $R^8$, $R^9$, —OR$^5$, —CONR$^5$R$^5$, —NR$^5$COR$^5$ or —NR$^5$R$^5$;

$R^{11}$ is phenyl optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, $C_1$–$C_6$ alkyl, halo(C$_1$–C$_6$)alkyl or $C_3$–$C_7$ cycloalkyl; and x is 0, 1 or 2.

\* \* \* \* \*